United States Patent [19]

Prather

[11] Patent Number: 5,404,887
[45] Date of Patent: Apr. 11, 1995

[54] GUIDE WIRE HAVING AN UNSMOOTH EXTERIOR SURFACE

[75] Inventor: Richard R. Prather, Rogers, Minn.

[73] Assignee: SciMed Life Systems, Inc., Maple Grove, Minn.

[21] Appl. No.: 147,724

[22] Filed: Nov. 4, 1993

[51] Int. Cl.$^6$ ............................................. A61B 5/02
[52] U.S. Cl. .................................. 128/772; 128/657
[58] Field of Search ................. 128/657, 672; 604/95, 604/164, 166, 170, 282, 280

[56] References Cited

U.S. PATENT DOCUMENTS

| | | | |
|---|---|---|---|
| 3,452,742 | 7/1969 | Muller | 128/2 |
| 3,731,671 | 5/1973 | Mageoh | 128/2.05 |
| 3,973,556 | 8/1976 | Fleischhacker et al. | 128/772 |
| 4,080,706 | 3/1978 | Heilman et al. | 128/772 X |
| 4,257,421 | 3/1981 | Beal | 128/772 X |
| 4,362,163 | 12/1982 | Krick | 604/280 |
| 4,430,083 | 2/1984 | Ganz et al. | 604/283 |
| 4,534,363 | 8/1985 | Gold | 128/772 |
| 4,579,127 | 4/1986 | Haacke | 128/772 |
| 4,682,607 | 7/1987 | Vaillancourt et al. | 128/772 |
| 4,811,743 | 3/1989 | Stevens | 128/772 |
| 4,884,579 | 12/1989 | Engelson | 128/772 |
| 5,107,852 | 4/1992 | Davidson et al. | 604/164 X |
| 5,122,125 | 6/1992 | Deuss | 604/282 |
| 5,125,909 | 6/1992 | Heimberger | 604/264 |
| 5,147,316 | 9/1992 | Castillenti | 604/164 |
| 5,147,317 | 9/1992 | Shank et al. | 604/164 |
| 5,228,453 | 7/1993 | Sepetka | 128/772 |
| 5,258,003 | 11/1993 | Ciaglia et al. | 604/164 X |

FOREIGN PATENT DOCUMENTS

| | | | |
|---|---|---|---|
| 2017182 | 10/1979 | United Kingdom | 128/772 |
| 93/04722 | 3/1993 | WIPO | 604/282 |

*Primary Examiner*—Sam Rimell
*Attorney, Agent, or Firm*—Nawrocki, Rooney & Silvertson

[57] ABSTRACT

A guide wire, and a method for the manufacture thereof, having an unsmooth surface along a segment thereof. According to one aspect of the invention, the unsmooth surface is provided by a sleeve member disposed about a distal portion of a core member. The sleeve member is formed from an extruded polymer and has an unsmooth exterior surface.

7 Claims, 4 Drawing Sheets

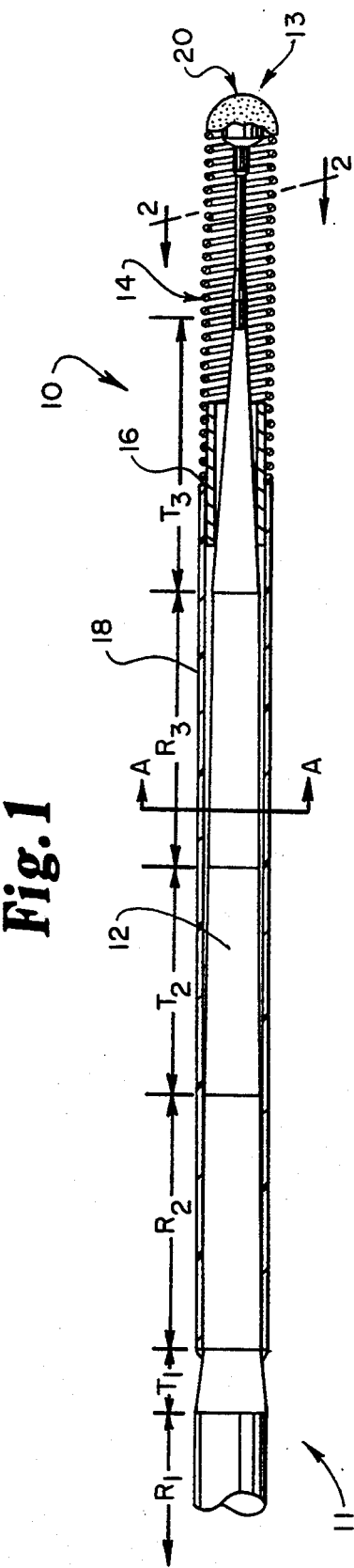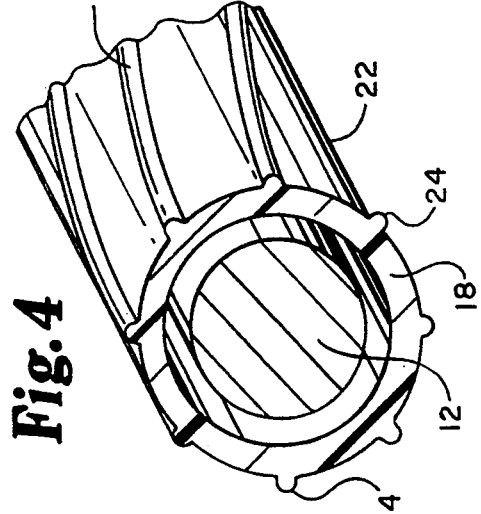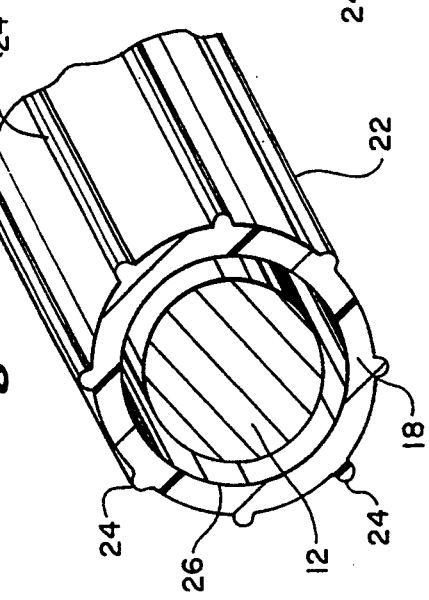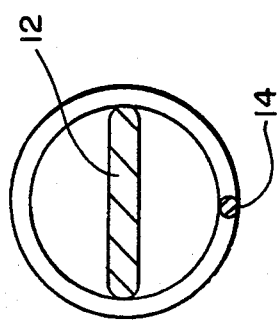

EXTRUDER

GUIDE WIRE HAVING AN UNSMOOTH EXTERIOR SURFACE

FIELD OF THE INVENTION

The present invention relates to intravascular guide wires, and methods of manufacture thereof. In particular, the present invention relates to an intravascular guide wire, and methods for the manufacture thereof, with improved properties to enhance the use thereof.

BACKGROUND OF THE INVENTION

Guide wires are used in various procedures in both the coronary regions and the peripheral regions of the body. For example, guide wires of a very small diameter, for example, on the order of 0.010 to 0.018 inches (0.26 to 0.46 mm), may be suitable for use in narrow coronary vessels. Such guide wires may have an extremely floppy distal tip which may be bent or preformed by the physician to facilitate placement of the guide wire at the desired location. Guide wires come in a range of sizes in addition to those discussed above.

Some of the characteristics preferred in guide wires by physicians include strength, the ability to provide a track for a balloon or other device to advance over and good torsional transmittance.

The size of the guide wire often affects the size and usefulness of devices used in conjunction therewith. For example, guide wires can be used in conjunction with dilation balloons used to perform angioplasty. One type of dilation catheter is referred to as an "over-the-wire" (OTW) catheter. An OTW catheter is one in which a guide wire lumen is provided in the catheter so that a guide wire can be used to establish the path through the stenoses. The dilation catheter can then be advanced over the guide wire until the balloon on the catheter is positioned within the stenoses.

There has been a continuing effort to reduce the profile and shaft size of the catheter so that the catheter can not only reach but also cross a very tight stenosis. Often this results in decreasing the diameter of the guide wire lumen of the catheter. In addition, the guide wire lumen as well as other parts of the catheter are made from polymers which allow a decrease in the wall thickness of the components while still providing the structural and mechanical characteristics needed. Portions of the guide wire may also be made from polymers. The polymer components on the guide wire may make intimate contact with the polymer generally used for the guide wire lumen of the catheter. This contact becomes greater as the difference between the two dimensions, the outer diameter of the guide wire and the inner diameter of the catheter lumen, decreases. The increasing surface contact and resulting polymer on polymer interactions can increase frictional resistance. Several attempts have been made to reduce friction between the guide wire and the guide wire lumen such as coating the exterior of the guide wire and/or the interior of the guide wire lumen with friction reducing materials such as TEFLON. See, U.S. Pat. Nos. 4,884,567 (Engelson) and 4,534,363 (Gold). Helical coils have also been used to reduce friction while providing greater flexibility and control. See U.S. Pat. Nos. 3,731,671 (Mageoh); 3,749,086 (Kline et al.) and 3,973,556 (Fleischhacker et al.). Other approaches can be found in U.S. Pat. Nos. 4,579,127 (Haacke) and 4,430,083 (Ganz et al.)

Accordingly, it is an object of the present invention to provide a guide wire that reduces the amount of contact between the guide wire and the guide wire lumen wall of a catheter used in conjunction with the guide wire.

SUMMARY OF THE INVENTION

According to a first aspect of the invention, there is provided a guide wire, and a method for the manufacture thereof, having a core member with a proximal and distal end and a sleeve member disposed about an exterior portion of the core member. The sleeve member has an unsmooth surface profile.

According to another aspect of the invention, there is provided in combination a catheter and guide wire. The catheter has an interior surface defining a guide wire lumen having generally a circular cross-section. The guide wire is slidably positioned in the guide wire lumen of the catheter. The guide wire has an exterior surface along a portion thereof which is at least partially in contact with the interior surface of the catheter. The exterior surface has a surface contour extending longitudinally therealong which has a shape such that there is a lesser amount of area in contact between the interior surface of the catheter and the exterior surface of the guide wire compared to an amount of area in contact between the interior surface of the catheter and the exterior surface of the guide wire if the exterior surface were circular in cross-section.

According to still another aspect of the invention, there is provided a guide wire, and a method for the manufacture thereof, having a core composed of a relatively rigid material. The core has a proximal portion having a relatively uniform cross section and a distal portion having at least one taper. An extruded polymer sleeve having an unsmooth exterior profile is connected to and surrounds at least a portion of the core.

BRIEF DESCRIPTION OF THE DRAWINGS

FIG. 1 illustrates a cross-sectional view of a guide wire according to the present invention.

FIG. 2 illustrates a cross sectional view of the guide wire of FIG. 1 taken along line 2—2.

FIG. 3 is a cross sectional view of the guide wire of FIG. 1 taken along line a—a according to a first embodiment of the present invention.

FIG. 4 is a cross sectional view of the guide wire of FIG. 1 taken along line a—a according to a second embodiment of the present invention.

DETAILED DESCRIPTION OF THE PRESENTLY PREFERRED EMBODIMENTS

Figure 5:
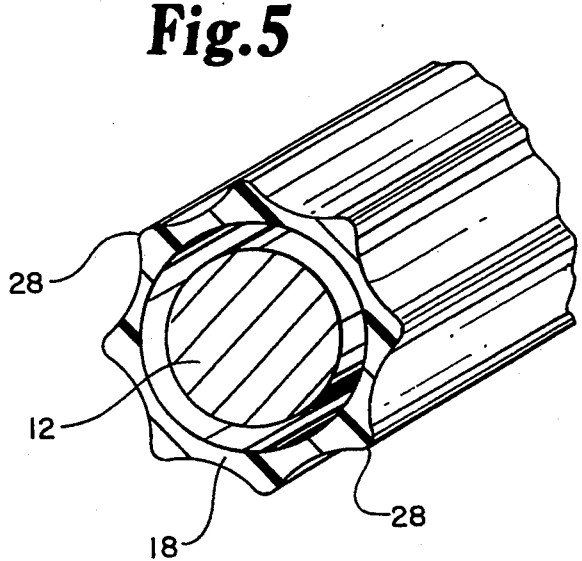
FIG. 5 is a cross sectional view of the guide wire of FIG. 1 taken along line a—a according to a third embodiment of the present invention.

FIG. 1 illustrates a cross-sectional view of a guide wire 10 according to the present invention. The guide wire 10 is designed preferably for intravascular use and more preferably for percutaneous transluminal coronary angioplasty (PTCA). This guide wire has a proximal end 11 and a distal end 13. The guide wire 10 includes a core member 12, a coil spring 14, a bridge member 16 and a sleeve member 18. In a preferred embodiment, the core member 12 is formed of stainless steel and has a proximal portion of substantially uniform diameter and a distal portion of reduced and tapered diameters. Other materials, including metals such as nitinol which are strong yet flexible may be used alone or in combination with other materials. The reduced and tapered diameters in the distal portion of the core member 12 provide greater flexibility to the distal portion of the guide wire 10. More specifically, the degree of flexibility in the distal portion of the guide wire 10 is determined by the number of tapers and the length and degree of each taper of the core member 12. The most distal portion of the core member 12 is flattened, i.e., preferably tapered from a circular cross-section to a rectangular or ribbon cross-section. The dimensions of the core member 12 as well as the dimensions of other parts of the guide wire 10 will be described in detail hereinafter.

The coil spring 14 surrounds the distal most portion of the core member 12. In a preferred embodiment, the coil spring 14 is composed of a radiopaque material and, most preferably, the coil spring 14 is composed of a platinum alloy having 92% platinum and 8% tungsten. The distal end of the coil spring 14 is connected to the distal end of the core member 12 by a ball weld 20 that forms a rounded distal tip. Other methods such as soldering may also be used to connect the distal end of the coil spring 14 to the distal end of the core member 12.

The sleeve member 18 surrounds a distal portion of the core member 12 proximal of the coil spring 14. In a preferred embodiment, the sleeve member 18 is positioned proximal to the coil spring 14 so that the distal end of the sleeve member 18 abuts the proximal end of the coil spring 14. The distal end of the sleeve member 18 and the proximal end of the coil spring 14 have substantially equal outer diameters so as to form a smooth transition between them. In a preferred embodiment, the sleeve member 18 is composed of a blend of nylon and polyether or polyether block amide, commercially available under the tradename PEBAX from Autochem of Birdsboro, Pa. Other materials such as polyester, polyurethane, polyimide and polytetrafluoroethylene (PTFE), for example may be used.

The bridge member 16 is located around the core member 12 under the distal end of the sleeve member 18 and the proximal end of the coil spring 14. In a preferred embodiment, the bridge member 16 is a small cylindrical hypotube of 304 stainless steel that fits around a portion of the core member 12. The outer diameter of the bridge member 16 corresponds to the inner diameters of the sleeve member 18 and the coil spring 14 as will be described in detail hereinafter. The bridge member 16 facilitates the alignment between the sleeve member 18 and the coil spring 14 over the core member 12.

The guide wire 10 may be constructed in various sizes to accommodate the specific environment in which it will be used. In a preferred embodiment, the guide wire 10 will have an overall outer diameter of either 0.014 or 0.018 inches (0.36 mm or 0.46 mm) and an overall length of about 74.8 inches (190 cm). The dimensions of the guide wire 10 having a diameter of about 0.014 inches (0.36 mm) will be described first. The following dimensional information is for illustration purposes and is not intended as a limitation of the preferred embodiments of the present invention. Guide wires having other dimensions may be constructed according to the present invention, in particular, smaller guide wires, for example, guide wires having a diameter of about 0.009 inches (0.23 mm) may be constructed.

As previously described, the core member 12 has several tapers along its length. Preferably, the tapers in the core member 12 are separated by regions of the core member 12 having a constant diameter. In a first region ($r_1$) having a length of about 60 inches (152.4 cm), the diameter of the core member 12 is about 0.0138 inches (0.351 mm). Adjacent to the first region ($r_1$) is a first taper ($t_1$) having a length of about 0.7 to about 1.3 inches (17.78 to 33.02 mm). In the first taper ($t_1$), the diameter of the core member 12 is reduced from the diameter of the first region ($r_1$), about 0.0138 inches (0.351 mm), to a diameter ranging from about 0.0064 to about 0.007 inches (0.1626 to 0.178 mm). Adjacent to the first taper ($t_1$) is a second region ($r_2$) having a length of about 6.75 to about 7.75 inches (17.15 to 19.69 mm) and a diameter of about 0.0064 to about 0.007 inches (0.1626 to 0.0178 mm). Adjacent to second region ($r_2$) is a second taper ($t_2$) having a length of about 0.7 to 1.3 inches (17.78 to 33.02 mm). In the second taper ($t_2$), the diameter of the core member 12 is reduced from the diameter of the second region ($r_2$), about 0.0064 to about 0.007 inches (0.1626 to 0.178 mm), to a diameter of about 0.0052 to about 0.0058 inches (0.132 to 0.147 mm). Adjacent to the second taper ($t_2$) is a third region ($r_3$) having a length of about 1.50 inches (38.1 mm) and a diameter of about 0.0042 to about 0.0058 inches (0.132 to 0.147 mm). Adjacent to third region ($r_3$) is a third taper ($t_3$) having a length of about 1.73 to about 1.77 inches (43.9 to 44.9 mm). In the third taper ($t_3$), the diameter of the core wire 10 is reduced from the diameter of the third region ($r_3$), about 0.0058 inches (0.132 to 0.147 mm), to a diameter of about 0.0023 to about 0.0027 inches (0.058 to 0.069 mm). There is a further reduction of the core wire accomplished by forming a ribbon having a flattened cross-section having a thickness of about 0.001 inches (0.026 mm) and a width of about 0.005 inches (0.13 mm) as will be described with reference to FIG. 2.

The cross-section of the core member in this region preferably changes from circular to rectangular. FIG. 2 illustrates a cross sectional view of the guide wire of FIG. 1 taken along line 2—2. The flattened portion has a length of about 0.48 to about 0.52 inches (12.2 to 13.2 mm), a thickness (t) of about 0.0009 to about 0.0013 inches (0.023 to 0.033 mm) and a width of about 0.005 inches (0.13 mm). The various regions of the core wire having tapers and sections of uniform cross section may be formed by methods known in the art, such as chemical washes, polishes, grinding or compressing for example.

The dimensions of the remaining parts of the guide wire 10 will now be described in detail. The coil spring 14 has a length of about 1.33 to about 1.43 inches (33.78 to 36.32 mm). The coil spring 14 is constructed of a wire having a diameter of about 0.0027 to about 0.0033 inches (0.069 to 0.084 mm) wound to form a coil having a pitch of about 0.0041 to about 0.0049 inches (0.104 to 0.125 mm). As previously described, the coil spring 14 is formed of a platinum alloy wire having 92% platinum and 8% tungsten. The bridge member 16 has a length of about 0.03 inches (0.76 mm), an outer diameter of about 0.0075 to about 0.0081 inches (0.19 to 0.21 mm) and an inner diameter of about 0.006 inches (0.15 mm). As previously described, the bridge member 16 is formed of 304 stainless steel. The sleeve member 18 will be described in detail with reference to FIGS. 3–7.

For a guide wire 10 with an overall diameter of about 0.018 inches (0.457 mm), the following changes in dimension are made to the dimensions described above with reference to the 0.014 inch guide wire. The diameter of the first region ($r_1$) is about 0.0178 inches (0.452 mm), the diameter of the second region ($r_2$) is about 0.0092 to about 0.0098 inches (0.234 to 0.249 mm). The distal end of the guide wire 10 has a diameter ranging from about 0.0175 to about 0.0185 inches (0.446 to 0.47 mm) and the bridge member 16 has an outer diameter of about 0.0115 to about 0.0121 inches (0.29 to 0.31 mm).

The sleeve member 18 has a length of about 10.5 to 11.0 inches (26.7 to 27.9 mm) and an inner diameter of about 0.009 inches (0.23 mm). The exterior surface profile of the sleeve member 18 is unsmooth as will be described with reference to FIGS. 3–7. Thus, the sleeve member 18 has a variable outer diameter which may range from a maximum outer diameter of about 0.014 inches (0.36 mm) and a minimum outer diameter of about 0.012 inches (0.30 mm).

While particular dimensions have been associated with the various components of the catheter, guide wires having other dimensions may be constructed and the present invention is not limited by the disclosed dimensions.

FIG. 3 is a cross sectional view of the guide wire 10 of FIG. 1 taken along line a—a according to a first embodiment of the present invention. In this embodiment, the unsmooth exterior surface 22 of the sleeve member 18 is created by ribs or nubs 24 formed on the exterior surface 22 of the sleeve member 18. In a preferred embodiment, the number of ribs 24 formed on the exterior surface 22 of the sleeve member 18 is determined by the surface area of the sleeve member 18 and the footprint of each rib 24. In a more preferred embodiment the number of ribs located around the periphery of the sleeve member 18 may range from four (4) to about sixteen (16). In a most preferred embodiment, eight (8) ribs are formed on the exterior surface 22 of the sleeve member 18 with each rib 24 uniformly spaced from adjacent ribs and each rib longitudinally extending parallel to the longitudinal axis of the core member 12. As previously described, the sleeve member 18 is preferably constructed of an extrudable material. The sleeve member is constructed by extruding the sleeve material through a die having a configuration or shape complementary to the exterior of the sleeve member 18 so that when the sleeve material is extruded through the die, ribs 24 are formed on its exterior surface 22. The inner surface 26 of the sleeve member 18 is smooth and preferably circular in cross-section.

Figure 12:
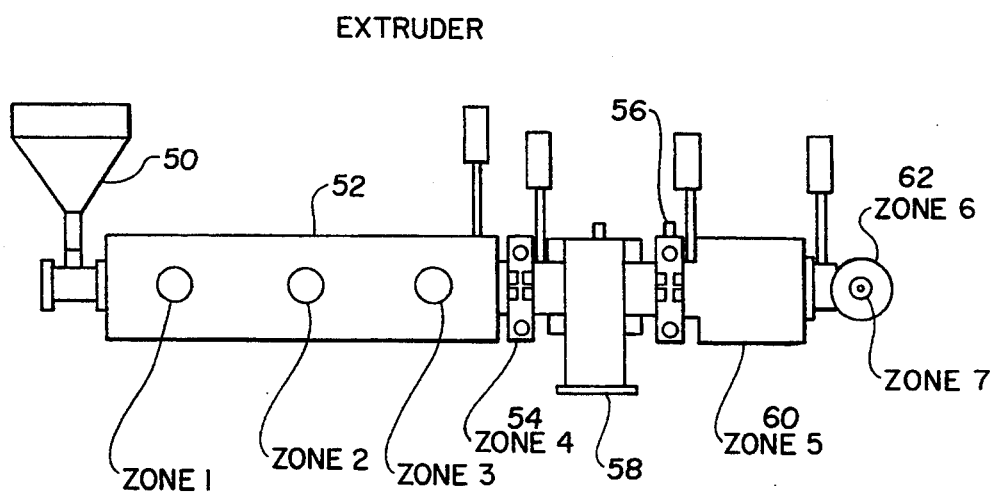
FIG. 12 is a schematic of an extruder.

FIG. 12 is a schematic of an extruder used to create a sleeve member according to the present invention. The extruder includes a hopper 50, a barrel 52, a first clamp ring 54 and a second clamp ring 56, a melt pump 58, a melt filter 60 and die 62. Temperature controllers (not shown) are used to control the temperatures in the various zones of the extruder. In a preferred embodiment zone 1 is set to a temperature of about 351° F., zone 2 is set to about 354° F., zone 3 is set to about 364° F., zone 4 is set to about 400° F., zone 5 is set to about 409° F., zone 6 is set to about 409° F. and zone 7 is set to about 412° F. After the temperature controllers have reached their set point, the extruder screw (not shown) is activated preferably at 4.5 revolutions per minute (rpm). Sleeve material is added to the hopper 50. The inlet pressure to the melt pump 58 is observed and once has increased from about 500 to about 1,000 psi, the melt pump 58 can be started. The pump 58 is started at about 2 rpm plus or minus 1 rpm. The pump 58 is run for about 10 to 15 minutes at this speed. Its speed can then be increased to about 15–20 rpm to fill the melt filter 60 with sleeve material. The melt pump 58 speed is adjusted to obtain a desired die pressure and output which will be explained in detail hereinafter. Once tubing is observed exiting the die 62, concentric bolts (not shown) located on the die are adjusted until the tubing lumen is concentric with the tubing outer diameter.

Next a puller and cutter assembly (not shown) is turned on and the speed of the puller is set to a reasonable speed so that when the extruded tubing goes into the puller it does not break off from the die face as is well known to those of ordinary skill in the art. Preferably the speed is set to approximately 125 feet per minute. The puller pulls the extruded tubing through a water bath positioned between the die face and the puller immediately after the die. The tubing extruded is then measured and if necessary adjustments are made in the puller speed.

FIG. 4 is a cross sectional view of the guide wire 10 of FIG. 1 taken along line a—a according to a second embodiment of the present invention. The sleeve member 18 of FIG. 4 is similar to that illustrated in FIG. 3, however, the ribs 24 do not extend longitudinally parallel to the longitudinal axis of the core member 12. Rather the ribs 24 form spirals along the exterior surface 22 of the sleeve member 18. To create the sleeve member of FIG. 4, the sleeve material is extruded through a die having the same shape as described with reference to FIG. 3 except the tubing or die is spun or twisted as it is extruded.

FIG. 5 is a cross sectional view of the guide wire 10 of FIG. 1 taken along line a—a according to a third embodiment of the present invention. In this embodiment, the cross section of the exterior surface of the sleeve member 18 is polygonal. Preferably the corners 28 of the polygon are rounded. In a most preferred embodiment, the cross section of the sleeve member 18 is octagonal with rounded corners. The sleeve member 18 according to this preferred embodiment is also formed by extruding the sleeve material through a die having a configuration complementary to the exterior surface of the sleeve member 18.

Figure 6:
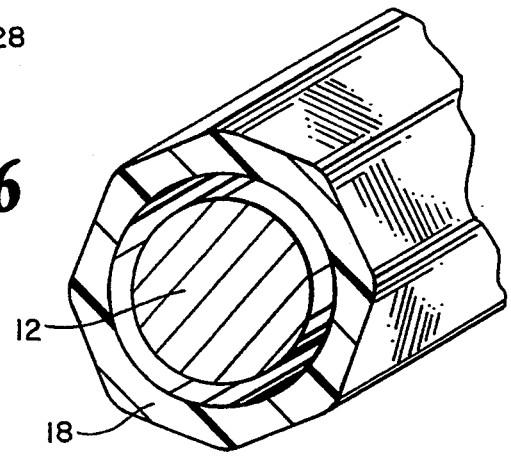
FIG. 6 is a cross sectional view of the guide wire of FIG. 1 taken along line a—a according to a fourth embodiment of the present invention.

FIG. 6 is a cross sectional view of the guide wire 10 of FIG. 1 taken along line a—a according to a fourth embodiment of the present invention. The sleeve member 18 of FIG. 6 is similar to that illustrated in FIG. 5 with the exception that the corners of the polygon are more rounded than those of FIG. 5. This can be accomplished by selecting a die having a configuration complementary to the exterior surface of the sleeve as previously described with reference to the other preferred embodiments or, the corners can be formed by extruding a sleeve member having the shape illustrated in FIG. 5 and then buffing the corners so that they become more rounded.

Figure 7:
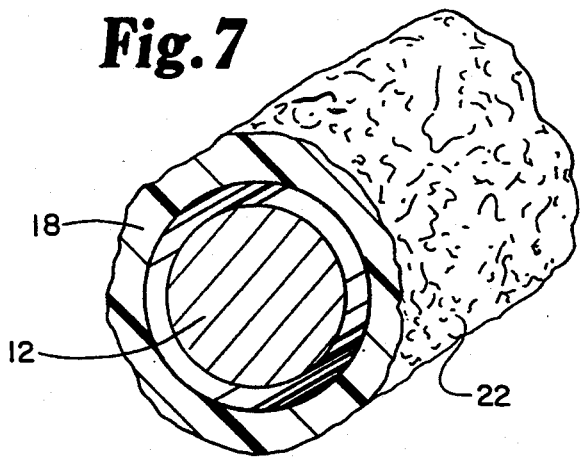
FIG. 7 is a cross sectional view of the guide wire of FIG. 1 taken along line a—a according to a fifth embodiment of the present invention.

FIG. 7 is a cross sectional view of the guide wire 10 of FIG. 1 taken along line a—a according to a fifth embodiment of the present invention. In this preferred embodiment, the sleeve member 18 is constructed from a piece of tubing initially having a smooth exterior surface 22. The exterior surface is then altered so that it becomes unsmooth. This may be accomplished by several methods. For example, an abrasive material may be rubbed along the exterior surface to form grooves in the surface of the sleeve member 18. Or the tubing may be placed in a cryogenic tumbler which causes the exterior surface to become unsmooth. Alternatively, the sleeve material may be extruded through a die having a smooth and preferably circular cross section but, as the tubing is extruded, air may be blown at the tubing thereby causing its surface to become unsmooth. Or the temperature of the extruder may be altered so that the outside surface of the extruded tube hardens before its inner surface thereby causing the exterior surface profile of the tubing to become irregular.

The construction of the guide wire 10 shown in FIG. 1 will now be described. The sleeve member 18 is loaded on the core member 12 and slid proximally. The bridge member 16 and coil spring 14 are then loaded on the core member 12. A weld is then formed at the distal end of the core member 12 to bond the distal end of the coil spring 14 with the distal end of the core wire and also to form the rounded tip 20. Forming such a weld is well known to those skilled in the art and this need not be described in detail. For a guide wire having an overall diameter of about 0.014 inches (0.36 mm), the rounded distal end 20 will have a diameter ranging from about 0.0135 to about 0.0145 inches (0.228 to 0.368 mm). The bridge member 16 is then positioned half way under the coil spring 14 and the coil spring 14 and bridge member 16 are soldered to the core member 12. The sleeve member 18 is then slid distally over the exposed half on the bridge member 16 and then bonded to the bridge member 16 at its distal end and the core member at its proximal end with LOCTITE 405 cyanoacrylate available from Loctite Corporation of Newington, Conn.

A coating may be applied to the distal 12 to 18 inches (40.6 to 45.7 cm) of the guide wire 10 approximately corresponding to the sleeve member 18 and the coil spring 14. In a preferred embodiment, the coating is composed of silicon oil and a modified moisture curable polydimethylsiloxane used on some commercially available devices sold by SciMed Life Systems, Inc., the assignee of the present invention, known under the tradename XTRA. The coating provides a uniform, low friction surface along the distal portion of the guide wire 10. Along the proximal portion of the guide wire 10 corresponding to the core member 12 proximal of the sleeve member 18, a coating of low friction material is applied, preferably Teflon. The low friction coating extends substantially the entire length of the proximal core member 12 from about 1.0 inch (25.4 mm) of the proximal end of the sleeve member 18 to within about 1.0 inch (25.4 mm) of the proximal end of the core member 12.

Figure 8:
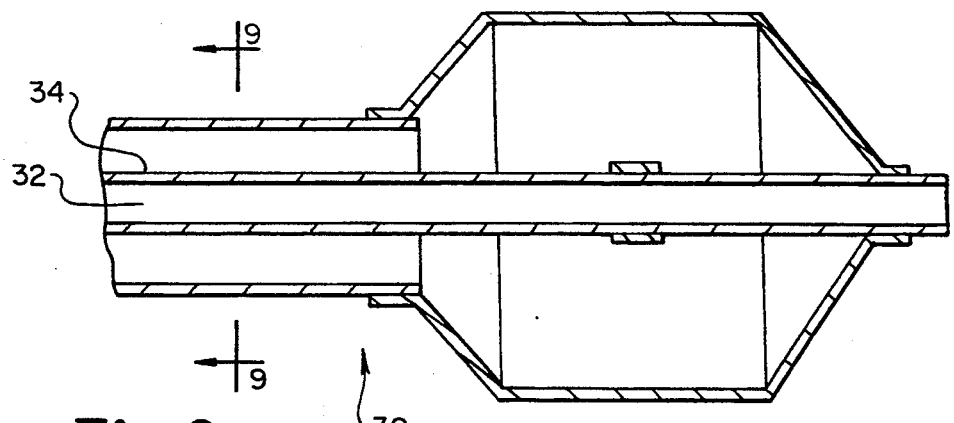
FIG. 8 illustrates an example of a first type of over-the-wire catheter.
Figure 9:
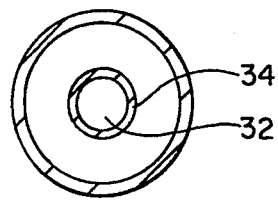
FIG. 9 is a cross sectional view of the catheter of FIG. 8 taken along line 9—9.
Figure 10:
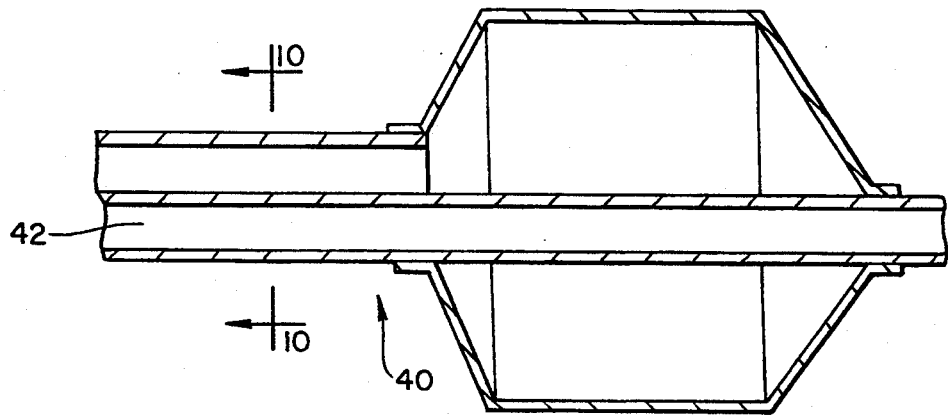
FIG. 10 illustrates an example of a second type of over-the-wire catheter.
Figure 11:
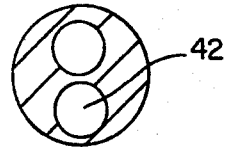
FIG. 11 is a cross sectional view of the catheter of FIG. 10 taken along line 11—11.

The preferred embodiments of the guide wire 10 described above may be used in combination with a catheter. Examples of two catheters that may be used with the guide wire 10 of the preferred embodiments are shown in FIGS. 8 and 10. FIG. 8 illustrates an example of a first type of over-the-wire catheter. The catheter 30 has a guide wire lumen 32 provided by inner tubular member 34. The guide wire lumen has a smooth circular cross section extending along its length as can be seen in FIG. 9 which is a cross-sectional view of the catheter of FIG. 8 taken along line 9—9. The catheter is conventional in design and thus need not be described in greater detail. FIG. 10 illustrates an example of a second type of over-the-wire catheter. The catheter 40 has a guide wire lumen 42 which preferably has a smooth circular cross section as can be seen in FIG. 11 which is a cross sectional view of the catheter of FIG. 10 taken along line 11—11. The catheter 40 is conventional in design and thus need not be described in greater detail. One suitable catheter which may be used with the guide wire of the present invention is commercially available under the tradename COBRA from SciMed Life Systems, Inc.

The guide wire 10 of the presently preferred embodiments has an unsmooth surface profile on at least a portion of its exterior so that when it is located within the guide wire lumen of the catheter 30 the exterior surface of the sleeve member 18 makes limited contact with the guide wire lumen wall. More specifically, the points of contact are made by the raised surface areas of the sleeve member 18 such as the ribs of FIGS. 3 and 4, the corner 28 of FIGS. 5 and 6 or the crests of the grooves of FIG. 7. Because the points of contact between the exterior surface of the sleeve member 18 and the guide wire lumen wall are less than would be the case if the exterior surface of the guide wire 10 were smooth, such as if it had a circular cross section, the amount of friction between the guide wire 10 and the guide wire lumen is reduced.

Figure 13:
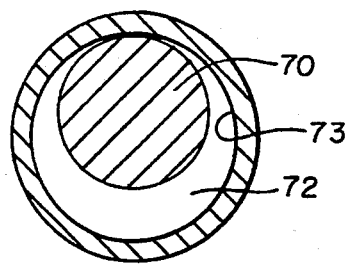
FIG. 13 illustrates a cross-sectional view of a guide wire having a smooth exterior surface in a lumen.
Figure 14:
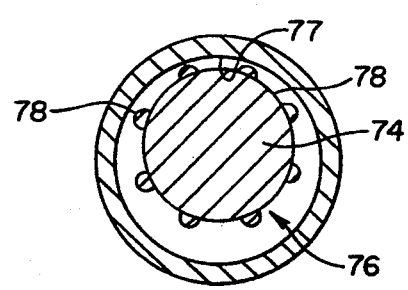
FIG. 14 illustrates a cross-sectional view of a guide wire according to the present invention in a lumen.

FIG. 13 illustrates a cross-sectional view of wire 70 having a smooth exterior surface in a lumen 72 such as the guide wire lumen of a catheter. In use the catheter bends as it travels through passageways, such as blood vessels, in the body thereby bringing the exterior of the guide wire in contact with the guide wire lumen wall 73 as shown in FIG. 13. Because the exterior surface of the guide wire is smooth, a large surface area of the guide wire contacts the guide wire lumen wall. FIG. 14 illustrates a cross-sectional view of a guide wire 74 according to the present invention in a guide wire lumen 76 of a catheter. Because the exterior surface of the guide wire 74 is unsmooth, the raised surfaces 78 limit the amount of contact between the exterior surface area of the guide wire 74 and the guide wire lumen wall 77. As can be clearly seen by comparing FIGS. 13 and 14, the guide wire according to the present invention reduces the amount of surface area contact between the exterior of the guide wire and the guide wire lumen wall. In addition, the sleeve according to the invention may be extended over a greater length of the core wire than illustrated in the preferred embodiments. In fact, the sleeve member could extend substantially the entire length of the core member if desired.

While the invention has been shown and described in connection with particular preferred embodiments, it is apparent that certain changes and modifications, in addition to those mentioned above, may be made by those who are skilled in the art without departing from the basic features of the present invention. Accordingly, it is the intention of the Applicant to protect all variations and modifications within the true spirit and valid scope of the invention.

What is claimed is:

1. A guide wire comprising:
   a core member having a proximal end and a distal end;
   a tubular sleeve member disposed about an exterior portion of said core member, said sleeve member located proximate the distal end of said guide wire and having a substantially smooth transition between said core member and said tubular sleeve member, wherein said sleeve member has an unsmooth exterior surface profile including a plurality of longitudinally extending circumferentially spaced ribs.

2. The guide wire of claim 1 wherein the core member is metallic.

3. The guide wire of claim 1 wherein the tubular sleeve member is manufactured from a polymeric material.

4. In combination, a catheter having an interior surface defining a guide wire lumen, said interior surface having generally a circular cross section; and
   a guide wire slidably positioned in said guide wire lumen of said catheter, said guide wire having an exterior surface along a length thereof, said exterior surface including a proximal portion and a distal portion, said proximal portion having a generally smooth exterior surface; and
   said exterior surface of said distal portion of said guide wire having a surface contour extending longitudinally therealong, said surface contour having a shape such that there is a lesser amount of area in contact between said interior surface of said catheter and said exterior surface of said portion of said guide wire compared to an amount of area in contact between said interior surface of said catheter and said exterior surface of said portion of said guide wire if said exterior surface were circular in cross-section, wherein said distal portion exterior surface is formed from a sleeve disposed over a core extending distally from said proximal portion and forming a substantially smooth transition between said proximal portion and said distal portion.

5. A catheter and guide wire according to claim 4 wherein said proximal portion exterior surface cross section is circular.

6. A catheter and guide wire according to claim 5 wherein said distal portion exterior surface cross-section is polygonal.

7. A catheter and guide wire according to claim 5 wherein said distal portion exterior surface cross-section is octagonal.

* * * * *